United States Patent
Hayakawa et al.

(10) Patent No.: US 9,132,266 B2
(45) Date of Patent: Sep. 15, 2015

(54) PROTECTOR AND METHOD FOR USING SAME

(71) Applicant: TERUMO KABUSHIKI KAISHA, Tokyo (JP)

(72) Inventors: Aya Hayakawa, Kanagawa (JP); Takemi Kobayashi, Tokyo (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/345,434

(22) PCT Filed: Sep. 24, 2012

(86) PCT No.: PCT/JP2012/074354
§ 371 (c)(1),
(2) Date: Mar. 18, 2014

(87) PCT Pub. No.: WO2013/047416
PCT Pub. Date: Apr. 4, 2013

(65) Prior Publication Data
US 2014/0358118 A1  Dec. 4, 2014

(30) Foreign Application Priority Data

Sep. 26, 2011  (JP) ................................. 2011-209517

(51) Int. Cl.
*A61M 39/28* (2006.01)
*A61M 5/32* (2006.01)
(Continued)

(52) U.S. Cl.
CPC .............. *A61M 39/28* (2013.01); *A61B 5/1405* (2013.01); *A61B 5/153* (2013.01);
(Continued)

(58) Field of Classification Search
CPC . A61M 39/28; A61M 39/281; A61M 5/1626; A61M 5/3202; A61M 5/3243; A61M 5/3271; A61M 39/283–39/287; A61M 2005/325; A61M 25/0612; A61M 25/0618; A61M 2039/1066; A61M 2005/3208; A61B 5/150534; A61B 5/150549; A61B 5/150587; A61B 5/150603; A61B 5/150633
See application file for complete search history.

(56) References Cited

U.S. PATENT DOCUMENTS 8,096,977 B2 *  1/2012  Ayiyama et al. .............. 604/171
2004/0249351 A1  12/2004  Hongo et al.

FOREIGN PATENT DOCUMENTS

JP  2000-342686 A  12/2000
JP  WO2004004805 A1  1/2004
(Continued)

OTHER PUBLICATIONS

International Search Report for International Application No. PCT/JP2012/074354, publication No. WO2013047416, mailed Oct. 16, 2012, issued by the Japanese Patent Office. (Japanese Language and English Translation included).

*Primary Examiner* — Bhisma Mehta
*Assistant Examiner* — James Ponton
(74) *Attorney, Agent, or Firm* — John R. Merkling

(57) ABSTRACT

A protector includes an outer tube and an inner tube. The outer tube includes an outer tube main body including an outer tube lumen for housing a puncture device, a holding part for holding a hub, and an extended part extended from the holding part. The inner tube includes an inner tube main body and a lumen inclined part. The inner tube main body is held in a proximal end side of the outer tube lumen and is movable in a proximal end direction of the outer tube lumen. The inner tube main body includes an inner tube lumen into which a tube is inserted. By moving the inner tube in a distal end direction, the inner surface of the lumen inclined part is abutted against the extended part, and the extended part is biased by the lumen inclined part in a direction in which a diameter of the tube is reduced.

6 Claims, 12 Drawing Sheets

(51) Int. Cl.
  *A61M 39/26* (2006.01)
  *A61B 5/15* (2006.01)
  *A61B 5/153* (2006.01)
  *A61B 17/34* (2006.01)
(52) U.S. Cl.
  CPC .... *A61B 5/150633* (2013.01); *A61B 5/150992* (2013.01); *A61M 5/3202* (2013.01); *A61M 39/26* (2013.01); *A61M 39/283* (2013.01); *A61M 39/284* (2013.01); *A61B 5/15003* (2013.01); *A61B 5/150221* (2013.10); *A61B 5/150259* (2013.01); *A61B 5/150389* (2013.01); *A61B 5/150503* (2013.01); *A61B 17/3496* (2013.01)

(56) References Cited

FOREIGN PATENT DOCUMENTS

| | | |
|---|---|---|
| JP | 2004-089674 A | 3/2004 |
| JP | 2007-89909 A | 4/2007 |

* cited by examiner

PROTECTOR AND METHOD FOR USING SAME

TECHNICAL FIELD

The present invention relates to a protector used by being attached to a puncture device and a method for using the same.

BACKGROUND ART

A blood collection, a blood transfusion and the like are performed by puncturing a blood vessel of a blood donor or a patient with a puncture device. Such a puncture device includes a needle tube with a sharp needle tip on a distal end, a hub connected to a proximal end part of the needle tube, and a tube connected to a proximal end part of the hub.

In a medical facility, contamination, infection, and the like through blood have been a problem. Especially, hepatitis B, hepatitis C, human immunodeficiency virus (HIV), and the like have been issues of public interest in a society. Thus, it is desired to actively prevent an erroneous puncture with a used puncture device.

Consequently, to prevent the erroneous puncture with a needle tip, the used puncture device is discarded with its needle tube and hub housed inside a protector and the like, so that the needle tip is not exposed, when a blood collection, a blood transfusion, and the like are finished.

For example, as the puncture device including such a protector, Patent Literature 1 describes a puncture device (medical needle device in the Literature) including a substantially cylindrical protector (shield tube in the Literature), a hub inserted into the shield tube to be movable in an axial direction and connected to a tube at a rear end part thereof, and a needle tube attached to a distal end part of the hub. A salient part is formed on an outer periphery of the distal end part of the hub. The salient part slides in a gate groove extended from a distal end of the shield tube to the vicinity of a rear end thereof in the axial direction. Thus, the needle tube is housed in the shield tube and the needle tip of the needle tube is not exposed.

CITATION LIST

Patent Literature

Patent Literature 1: JP 3536847 B1

SUMMARY OF INVENTION

Technical Problem

In a conventional puncture device including a protector, a needle tube is housed in the protector. Thus, an erroneous puncture with a needle tip is prevented. Also, contamination, infection, and the like through blood are occurring less often. However, the conventional puncture device including the protector may have the following problem. That is, blood remaining in a tube may leak and be scattered from a distal end opening of the protector, when the puncture device is discarded. Thus, the contamination, the infection and the like through the blood are deeply feared.

Accordingly, the present invention has been made to solve these problems. An object thereof is to provide a protector and a method for using the same, which reliably prevent a leak and a scatter of blood from the protector when discarding a puncture device after a blood collection, a blood transfusion and the like are finished, and make it possible to decrease contamination, infection, and the like through the blood.

Solution to Problem

To solve the problem, a protector according to claim 1 of the present invention is configured to be used by being attached to a puncture device including a needle tube which includes a needle tip on a distal end side thereof, a hub provided to a proximal end side of the needle tube, and a tube connected to a proximal end side of the hub and communicating with the needle tube through the hub. The protector is movable in a longitudinal direction of the tube and includes an outer tube and an inner tube. The outer tube includes: a tubular outer tube main body which includes an outer tube lumen configured to house the puncture device; a holding part configured to hold the hub in the outer tube lumen to house the needle tip in the outer tube lumen; and at least one extended part which is extended from a proximal end side of the holding part in a proximal end direction of the outer tube lumen. The inner tube includes: a tubular inner tube main body which is held in the proximal end side of the outer tube lumen and movable in a distal end direction of the outer tube lumen and includes an inner tube lumen into which the tube is inserted; and a lumen inclined part in which an inner diameter of the inner tube lumen gradually increases toward a distal end side of the inner tube main body. When the puncture device is housed in the outer tube lumen, the inner tube is moved in a distal end direction of the outer tube, whereby an inner surface of the lumen inclined part is abutted against the extended part and the extended part is biased by the lumen inclined part in a direction in which a diameter of the tube is reduced.

According to the configuration above, when the puncture device is housed in the outer tube lumen of the outer tube, preferably after the puncture device is held in the outer tube lumen, the inner tube is moved in the distal end direction of the outer tube. Thus, the inner surface of the lumen inclined part is abutted against the at least one extended part, and the extended part is biased by the lumen inclined part in the direction in which the diameter of the tube is reduced. As a result, the tube is occluded, and the leak and the scatter of the blood remaining in the tube from a distal end side of the outer tube main body can be prevented when the puncture device is discarded after the blood collection, the blood transfusion, and the like are finished. In addition, since the outer tube includes the outer tube main body including the outer tube lumen to house the puncture device, and the holding part which holds the hub in the outer tube lumen to house the needle tip in the outer tube lumen, the erroneous puncture with the puncture device can be prevented.

A protector according to claim 2 of the present invention is configured to be used by being attached to a puncture device including a needle tube which includes a needle tip on a distal end side thereof, a hub provided to a proximal end side of the needle tube, and a tube connected to a proximal end side of the hub and communicating with the needle tube through the hub. The protector is movable in a longitudinal direction of the tube and includes an outer tube, a first inner tube, and a second inner tube. The outer tube includes: a tubular outer tube main body which includes an outer tube lumen configured to house the puncture device; and a holding part configured to hold the hub in the outer tube lumen to house the needle tip in the outer tube lumen. The first inner tube includes: a tubular first inner tube main body which is held in a proximal end side of the outer tube lumen and movable in a proximal end direction of the outer tube lumen and includes an inner tube lumen into which the tube is inserted; and a lumen inclined part in which an inner diameter of the inner tube lumen gradually increases toward a distal end side of the first inner tube main body. The second inner tube includes: a tubular second inner tube main body which is held in the outer tube lumen in a distal end direction of the first inner tube and movable in the distal end direction of the outer tube lumen and into which the tube is inserted; and at least one extended part extended from a proximal end side of the second inner tube main body in the proximal end direction of the outer tube lumen. When the puncture device is housed in the outer tube lumen, the first inner tube is moved in a distal end direction of the outer tube, whereby the second inner tube is moved in the distal end direction of the outer tube and abutted against the holding part, an inner surface of the lumen inclined part is abutted against the extended part, and the extended part is biased by the lumen inclined part in a direction in which a diameter of the tube is reduced.

According to the configuration above, when the puncture device is housed in the outer tube lumen of the outer tube, preferably after the puncture device is held in the outer tube lumen, the first inner tube is moved in the distal end direction of the outer tube. Thus, the second inner tube is moved in the direction toward the distal end of the outer tube and abutted against the holding part, the inner surface of the lumen inclined part is abutted against the at least one extended part, and the extended part is biased by the lumen inclined part in the direction in which the diameter of the tube is reduced. As a result, the tube is occluded, and the leak and the scatter of the blood remaining in the tube from a distal end side of the outer tube main body can be prevented when the puncture device is discarded after the blood collection, the blood transfusion, and the like are finished. In addition, since the outer tube includes the outer tube main body including the outer tube lumen to house the puncture device, and the holding part which holds the hub in the outer tube lumen to house the needle tip in the outer tube lumen, the erroneous puncture with the puncture device can be prevented.

A method for using a protector according to claim 3 of the present invention is a method for using the protector of claim 1. The method includes: a first step in which the puncture device is housed in the outer tube lumen; a second step in which the puncture device is held in the outer tube lumen; a third step in which the inner tube is moved in the distal end direction of the outer tube, with the puncture device housed in the outer tube lumen; a fourth step in which the extended part is abutted against the inner surface of the lumen inclined part after the inner tube is moved in the distal end direction of the outer tube, and then the extended part is biased along with and by the lumen inclined part in the direction in which the diameter of the tube is reduced; and a fifth step in which the tube is deformed and a lumen of the tube is occluded by the extended part being biased in the direction in which the diameter of the tube is reduced.

According to the procedure above, the tube is occluded, and the leak and the scatter of the blood remaining in the tube from a distal end side of the outer tube main body can be prevented when the puncture device is discarded after the blood collection, the blood transfusion, and the like are finished. In addition, since the needle tip is housed in the outer tube lumen, the erroneous puncture with the puncture device can be prevented.

A method for using a protector according to claim 4 of the present invention is a method for using the protector of claim 2. The method includes: a first step in which the puncture device is housed in the outer tube lumen; a second step in which the puncture device is held in the outer tube lumen; a third step in which the first inner tube is moved in the distal end direction of the outer tube, with the puncture device housed in the outer tube lumen, to move the second inner tube in the distal end direction of the outer tube; a fourth step in which the extended part is abutted against the inner surface of the lumen inclined part after the second inner tube is moved in the distal end direction of the outer tube, and then the extended part is biased along with and by the lumen inclined part in the direction in which the diameter of the tube is reduced; and a fifth step in which the tube is deformed and a lumen of the tube is occluded by the extended part being biased in the direction in which the diameter of the tube is reduced.

According to the procedure above, the tube is occluded, and the leak and the scatter of the blood remaining in the tube from a distal end side of the outer tube main body can be prevented when the puncture device is discarded after the blood collection, the blood transfusion, and the like are finished. In addition, since the needle tip is housed in the outer tube lumen, the erroneous puncture with the puncture device can be prevented.

Advantageous Effects of Invention

By a protector and a method for using the same according to the present invention, when discarding a puncture device after a blood collection, a blood transfusion, and the like are finished, a leak and a scatter of blood from the protector can be reliably prevented, and an erroneous puncture with the puncture device can also be prevented. Therefore, contamination, infection, and the like through blood can be further decreased, compared to the conventional protector.

DESCRIPTION OF EMBODIMENTS

First Embodiment of Protector

A first embodiment of a protector according to the present invention will be described in detail with reference to the drawings.

Figure 1:
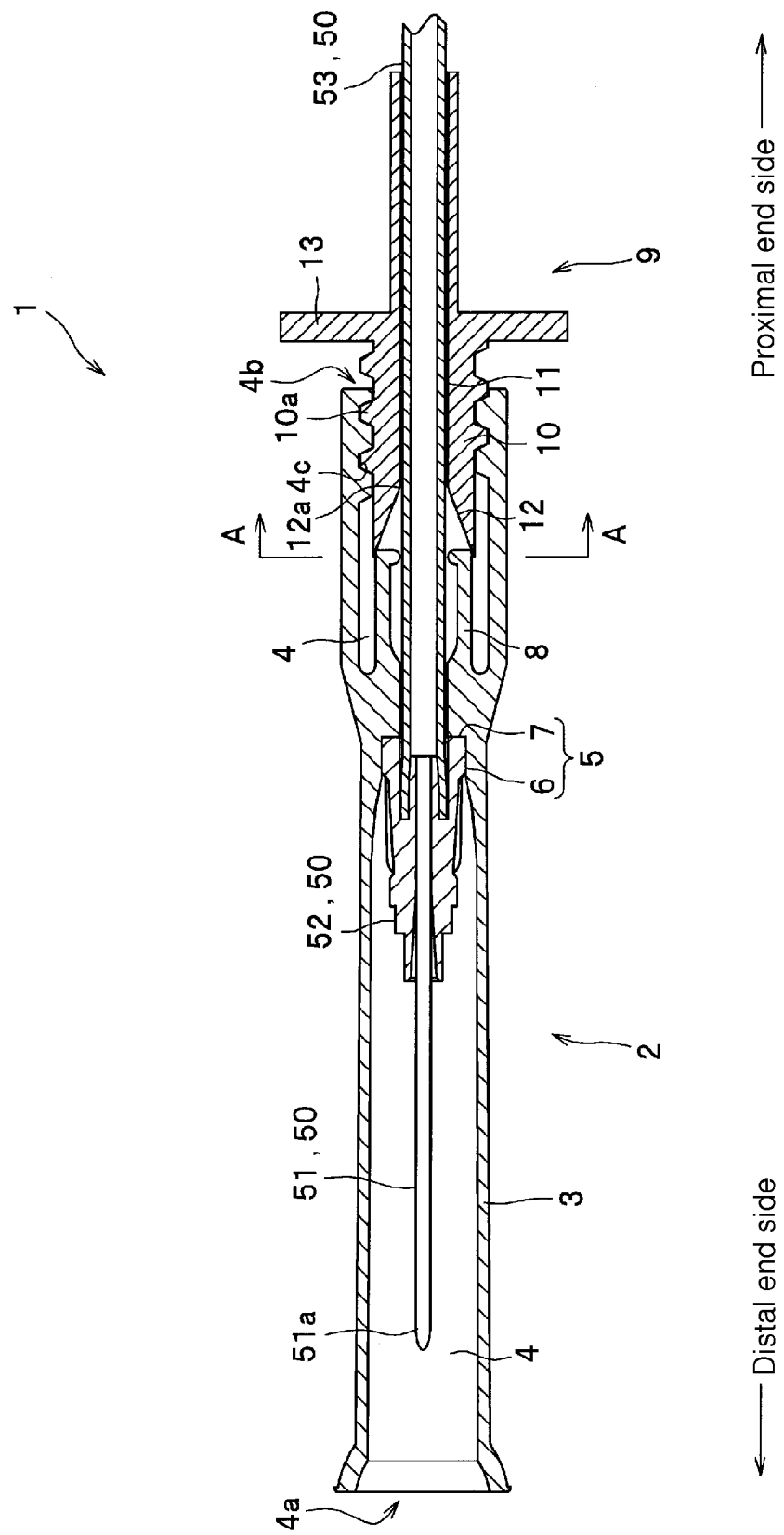
FIG. 1 is a vertical sectional view showing a configuration of a protector according to a first embodiment before an occlusion of a tube.
Figure 12:
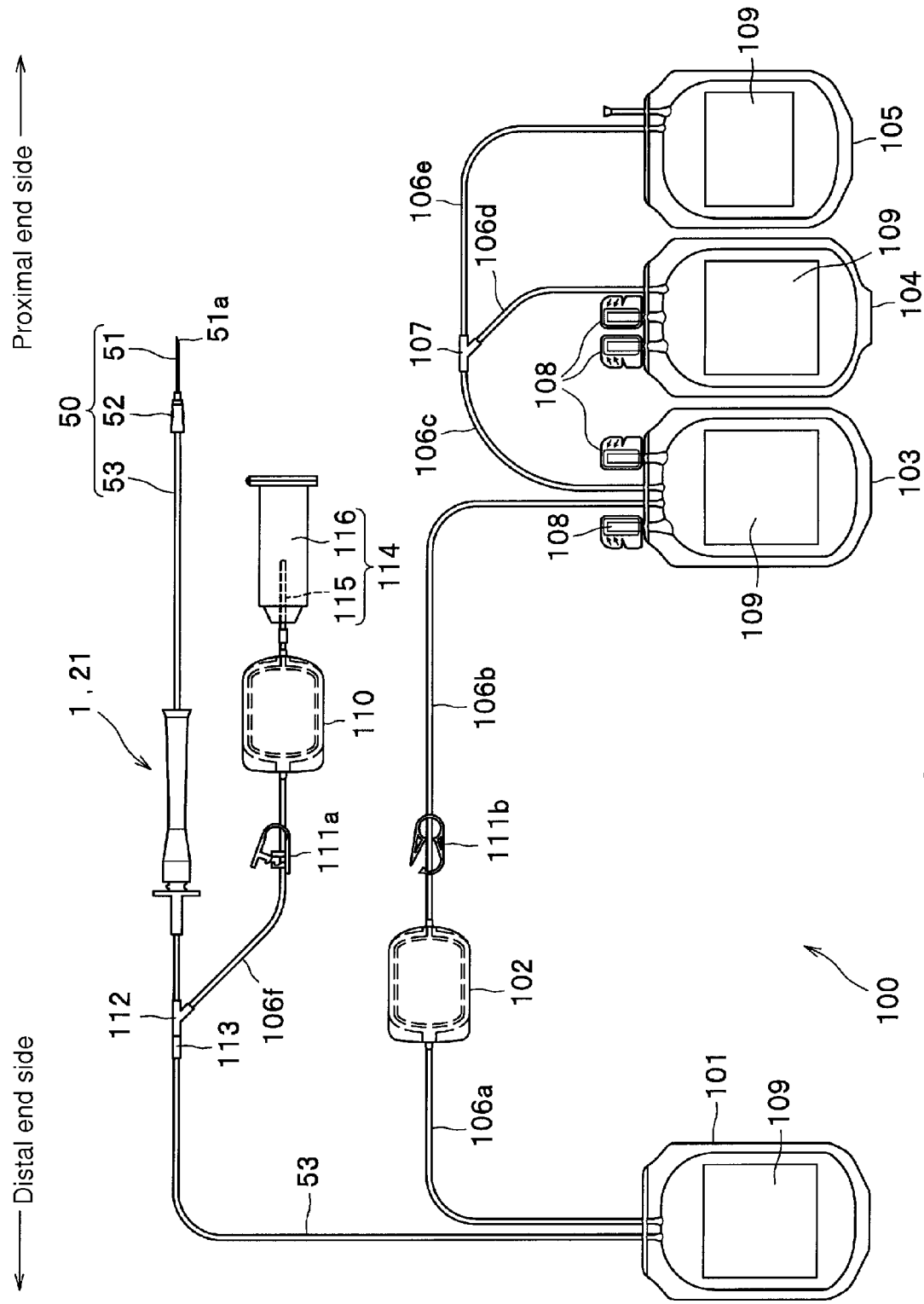
FIG. 12 is a schematic view showing a configuration of a blood bag system.

As shown in FIGS. 1 and 12, a protector 1 in the first embodiment is used by being attached to a puncture device 50. Before describing the protector 1, the puncture device 50 to which the protector 1 is attached will be described.

Note that in the present invention, a distal end side (distal end direction) means the side of a blood donor or a patient (patient direction) to be punctured with a puncture device in the case of a blood collection or a blood transfusion, and a proximal end side (proximal end direction) means the side of a medical device (medical device direction) in and out of which blood flows in the case of the blood collection or the blood transfusion, such as the side of a blood bag system (blood bag system direction).

(Puncture Device)

As shown in FIG. 12, the puncture device 50 is used to puncture a blood vessel of a blood donor or a patient in the case of a blood collection or a blood transfusion. The puncture device 50 includes a needle tube 51, a hub 52, and a tube 53.

The needle tube 51 includes a metal material such as stainless steel, and a sharp needle tip 51a is formed on a distal end side thereof. The shape of the needle tip (blade edge) 51a is not particularly limited. The needle tip 51a includes a blade surface inclined toward an axis of the needle tube 51 at a prescribed angle.

The hub 52 is provided on a proximal end side of the needle tube 51. The hub 52 is a tubular body including a synthetic resin, and liquid-tightly fixed to the needle tube 51 by fitting, caulking, fusion welding, gluing with an adhesive, or the like. The hub 52 communicates with the inside of the needle tube 51. Also, a cross-sectional shape (sectional shape in a direction orthogonal to the axis) of the hub 52 is preferably circular (including oval), square, or the like, but not particularly limited thereto. In addition, the hub 52 preferably includes a transparent resin which secures visibility of the inside. With this configuration, inflow of the blood (flashback) into the hub 52 can be visually confirmed, when the blood vessel is secured. Also, the hub 52 may be a winged hub which includes a tabular wing part extended from an outer periphery thereof in the direction orthogonal to the axis, although not shown in the figures. With the wing part, it becomes easier to fix the hub 52 to the skin of the blood donor or the patient.

The tube 53 includes a synthetic resin having flexibility. Also, a distal end side of the tube 53 is liquid-tightly connected to a proximal end side of the hub 52 by fitting, gluing, or the like. The distal end side of the tube 53 communicates with the needle tube 51 through the hub 52. Thus, it becomes possible for the blood to pass from the needle tube 51 to the tube 53, or to pass from the tube 53 to the needle tube 51. Furthermore, a proximal end side of the tube 53 is connected to a blood collecting bag 101 of a blood bag system 100 and the like.

In addition, a cap is attached on the needle tube 51 when the puncture device 50 is not yet used, although not shown in the figures. The cap includes a synthetic resin and the like, and covers the needle tip 51a. Since the needle tip 51a is covered with the cap, an erroneous puncture with the puncture device 50 (needle tip 51a) can be prevented.

The protector 1 used by being attached to the puncture device 50 described above is movable in a longitudinal direction of the tube 53. The movable protector 1 means that the protector 1 may take a first condition and a second condition. In the first condition, the protector 1 is placed on the proximal end side of the hub 52 and spaced from the needle tube 51 and the hub 52, as shown in FIG. 12. In the second condition, the protector 1 houses, preferably holds, the tube 53 and the hub 52 inside, as shown in FIG. 1.

Figure 2:
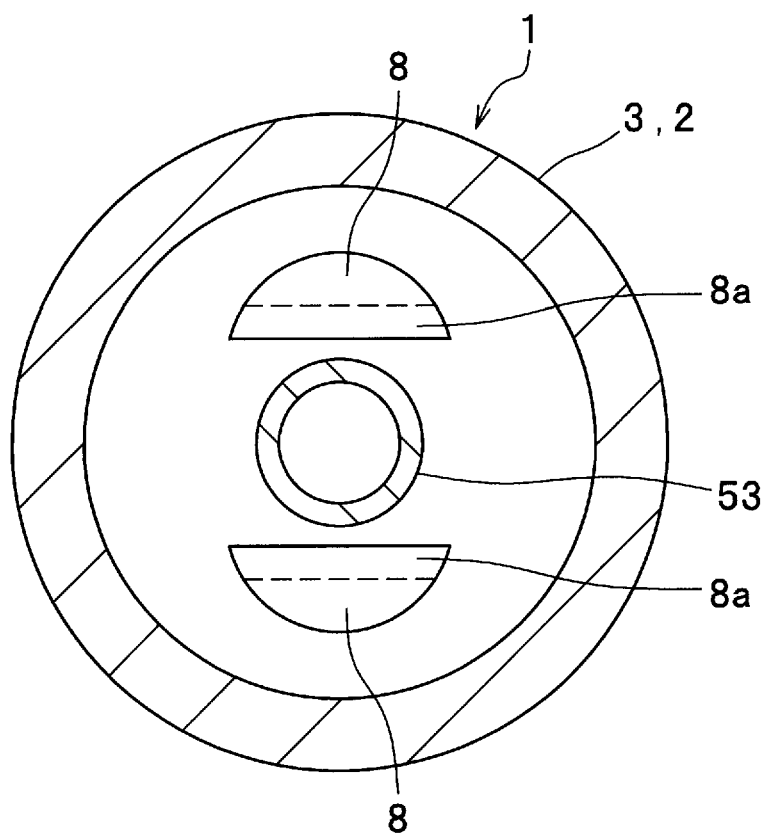
FIG. 2 is an A-A sectional view of FIG. 1.

As shown in FIGS. 1 and 2, the protector 1 includes an outer tube 2 and an inner tube 9.

A material for the outer tube 2 and the inner tube 9 is not particularly limited but can include, for example, polyolefin such as polyethylene, polypropylene, and ethylene-vinyl acetate copolymer, and various synthetic resin materials such as polycarbonate. In the following, each of the configurations will be described.

(Outer Tube)

The outer tube 2 includes an outer tube main body 3, a holding part 5, and an extended part 8.

The outer tube main body 3 includes a tubular body in which an outer tube lumen 4 is formed. Both ends of the outer tube lumen 4 are opened, that is, the outer tube lumen 4 includes a distal end opening 4a and a proximal end opening 4b. The outer tube lumen 4 houses the puncture device 50 inside. In addition, the outer tube main body 3 functions as a grip to be gripped by a user when the protector 1 is moved from the first condition to the second condition. Therefore, to prevent the outer tube main body 3 from slipping when gripped, on an outer surface of the outer tube main body 3, a plurality of recess parts or salient parts formed in a direction of an outer periphery thereof (direction orthogonal to the axis) is preferably provided in a longitudinal direction (direction along the axis), although not shown in the figures. Furthermore, although not shown in the figures, the outer tube main body 3 may include a groove extended in the axial direction from the distal end opening 4a to the vicinity of the holding part 5 described later. With the groove, the wing of the winged hub can slide in the groove, and the winged hub can be housed and held in the outer tube main body 3.

A cross-sectional shape of the outer tube main body 3 is preferably circular (including oval), square, or the like, to achieve the better operability in the movement of the protector 1, but not particularly limited. Also, a cross-sectional shape of the outer tube lumen 4 is preferably circular (including oval), square, or the like, to improve the housing capability of the puncture device 50, but not particularly limited. Furthermore, a vertical sectional shape (sectional shape in the axial direction) of the outer tube lumen 4 is preferably a taper shape, an inner diameter of which gradually increases from the holding part 5 described in the following toward the distal end opening 4a. This makes it easier to house the puncture device 50 in the outer tube lumen 4.

The holding part 5 holds the hub 52 in the outer tube lumen 4 to house the needle tip 51a of the puncture device 50 in the outer tube lumen 4. The position of the holding part 5 in the outer tube lumen 4 is appropriately set to keep the distance between the distal end opening 4a and the holding part 5 equal to or longer than the length of the needle tube 51. The configuration of the holding part 5 is not particularly limited as long as the hub 52 can be held, but the holding part 5 includes either a reduced diameter part 6 or a step 7, and preferably includes both.

The reduced diameter part 6 means a part in which an inner diameter of the outer tube lumen 4 is reduced to be the same as an outer diameter of the hub 52. Note that the outer diameter of the hub 52 means a diameter when the hub 52 includes a circular cross section, and means a short outer diameter when the hub 52 includes a square cross section. In the reduced diameter part 6, the hub 52 is held in the outer tube lumen 4 by the friction between an inner periphery of the outer tube main body 3 (outer tube lumen 4) and the outer periphery of the hub 52.

The step part 7 is a protruded part which protrudes into the inside of the outer tube lumen 4 to make the inner diameter of the outer tube lumen 4 smaller than the outer diameter of the hub 52. Specifically, the step part 7 is a part in which the thickness of the outer tube main body 3 is increased. The step part 7 holds the hub 52 on an end surface of a distal end side thereof.

The extended part 8 is extended from a proximal end side of the holding part 5 in a proximal end direction of the outer tube lumen 4, specifically, toward a lumen inclined part 12 of an inner tube 9 described later. At least one extended part 8 is formed on an end surface peripheral rim of a proximal end side of the step part 7 (holding part 5). Multiple extended parts 8 are preferably formed at regular intervals. As described later, the extended part 8 is abutted against the inner surface of the lumen inclined part 12 by the movement of the inner tube 9 and is biased by the lumen inclined part 12 in a direction in which the diameter of the tube 53 is reduced. Preferably, the number of the extended parts 8 is two, formed to face each other with the tube 53 there between. The number of the extended parts 8 is not limited to two, and can be more than two, such as three or four, as long as the tube 53 is deformed in the direction in which the diameter thereof is reduced, and the tube 53 is occluded.

The length of the extended part 8 is appropriately set to the length which enables the extended part 8 to be abutted against the inner surface of the lumen inclined part 12 and biased by the lumen inclined part 12, to deform the tube 53 in the direction in which the diameter of the tube 53 is reduced, and to occlude the tube 53. In addition, to secure the occluded condition of the tube 53, it is preferable to set the length of the extended part 8 appropriately such that the position of a distal end of the extended part 8 is arranged closer to the distal end side than a proximal end 12a of the lumen inclined part 12 when the tube 53 is occluded.

Here, the occluded condition of the tube 53 means that the blood flow channel of the tube 53 is blocked. In other words, this means that the outer diameter of the tube 53 is reduced to twice the thickness thereof (see FIG. 4).

Figure 5A:
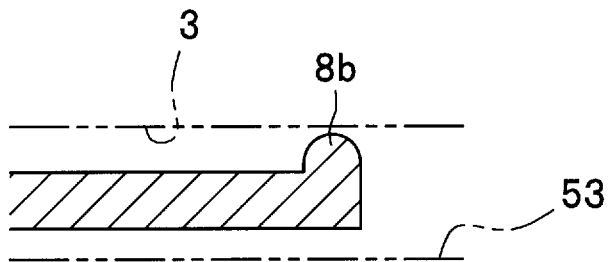
FIGS. 5(*a*) and 5(*b*) are vertical sectional views showing other shapes of distal ends of extended parts.
Figure 5B:
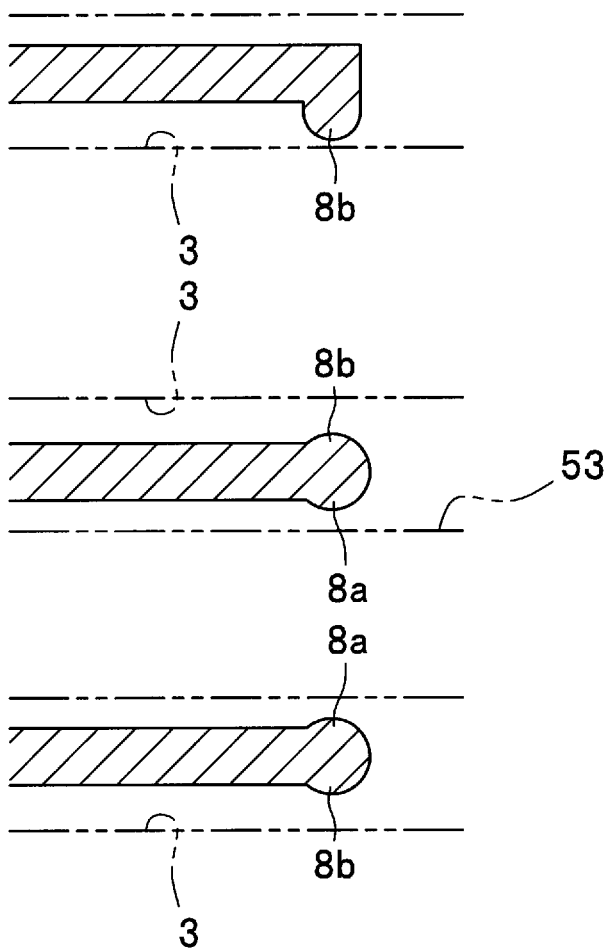

Preferably, the distal end of the extended part 8 includes a protruded part 8a which protrudes to the side of the tube 53. As shown in FIGS. 5(a) and 5(b), the extended part 8 may include a protruded part 8b which protrudes to the side of the outer tube main body 3 (see FIG. 5(a)), or may include both of the protruded part 8a and the protruded part 8b (see FIG. 5(b)).

(Inner Tube)

The inner tube 9 includes an inner tube main body 10 and the lumen inclined part 12.

The inner tube main body 10 includes a tubular body in which an inner tube lumen 11 is formed. Both ends of the inner tube lumen 11 are open, and the tube 53 is inserted into the inner tube lumen 11. The inner tube main body 10 is held in the proximal end side (side of proximal end opening 4b) of the outer tube lumen 4. Also, the inner tube main body 10 is movable in a distal end direction of the outer tube lumen 4, specifically, toward the side of the extended part 8. To make the inner tube main body 10 movable to the side of the extended part 8, it is preferable to form a male screw 10a on an outer periphery of the inner tube main body 10 and to form a female screw 4c in an inner periphery of the outer tube main body 3. The male screw 10a is screwed into the female screw 4c. Although not shown in the figures, a female screw may be formed in the outer periphery of the inner tube main body 10, and a male screw may be formed on the inner periphery of the outer tube main body 3. In addition, the male screw 10a and the female screw 4c may not be formed as long as the inner tube main body 10 is held in the outer tube lumen 4 and can be moved to the side of the extended part 8. Instead, the inner tube main body 10 may be held by surface contact between the outer periphery of the inner tube main body 10 and the inner periphery of the outer tube main body 3. Furthermore, to make it easier for the inner tube main body 10 to move toward the side of the extended part 8, the inner tube main body 10 preferably includes an operation part 13 having a prescribed length. The operation part 13 is installed upright on a proximal end side of the inner tube main body 10 in a direction orthogonal to the axis.

The lumen inclined part 12 is formed in the inner tube main body 10. The lumen inclined part 12 is a part in which the inner diameter of the inner tube lumen 11 gradually increases toward a distal end of the inner tube main body 10 (toward the side of the extended part 8). An inclination angle of the inner tube lumen 11 at the lumen inclined part 12 is appropriately set by considering the inner diameter of the inner tube lumen 11 and the outer diameter and the thickness of the tube 53, to make it possible to bias the at least one extended part 8 and to deform the tube 53 with the extended part 8 in the direction in which the diameter of the tube 53 is reduced.

Figure 3:
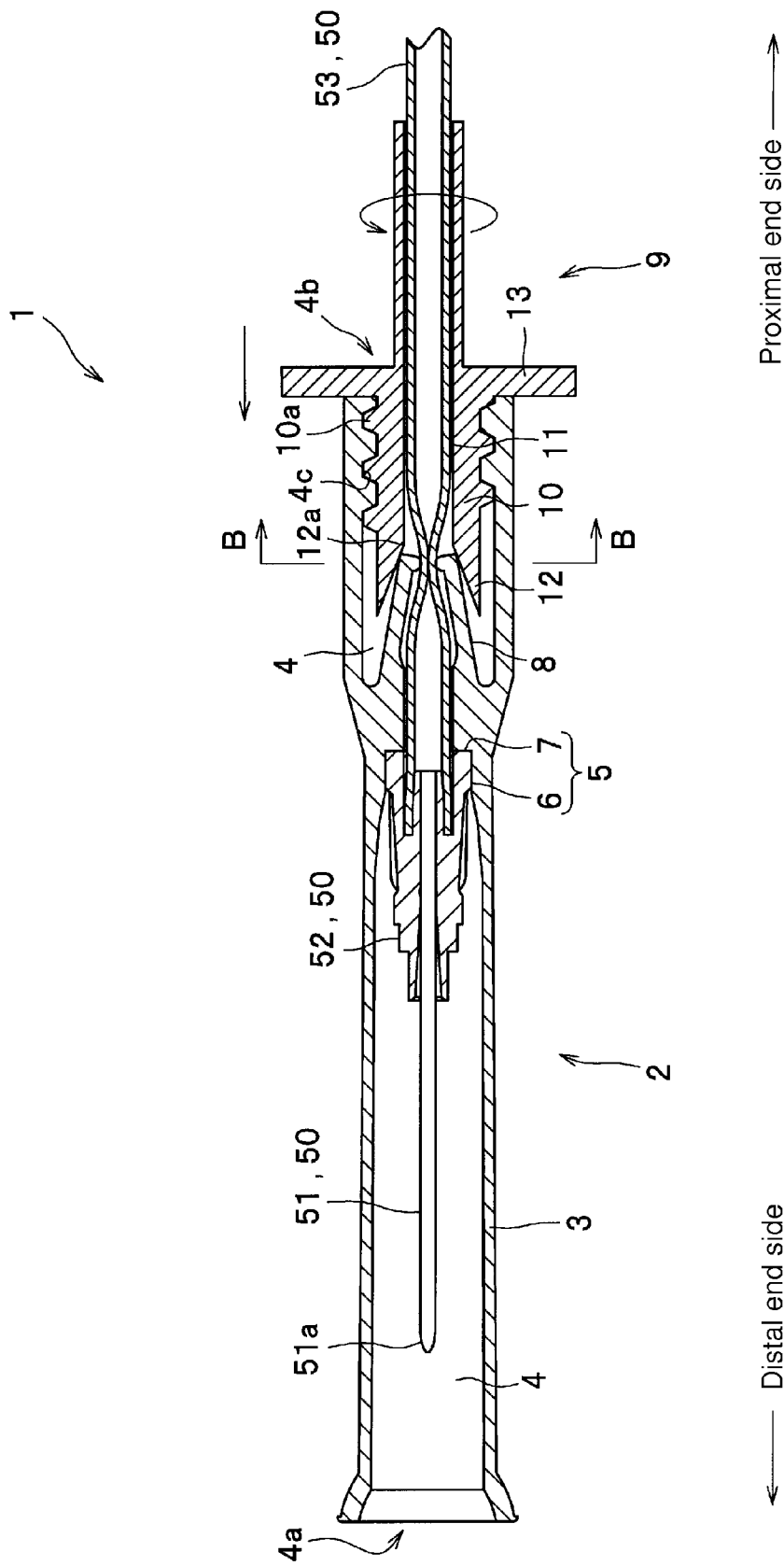
FIG. 3 is a vertical sectional view showing a configuration of the protector according to the first embodiment after the occlusion of the tube.
Figure 4:
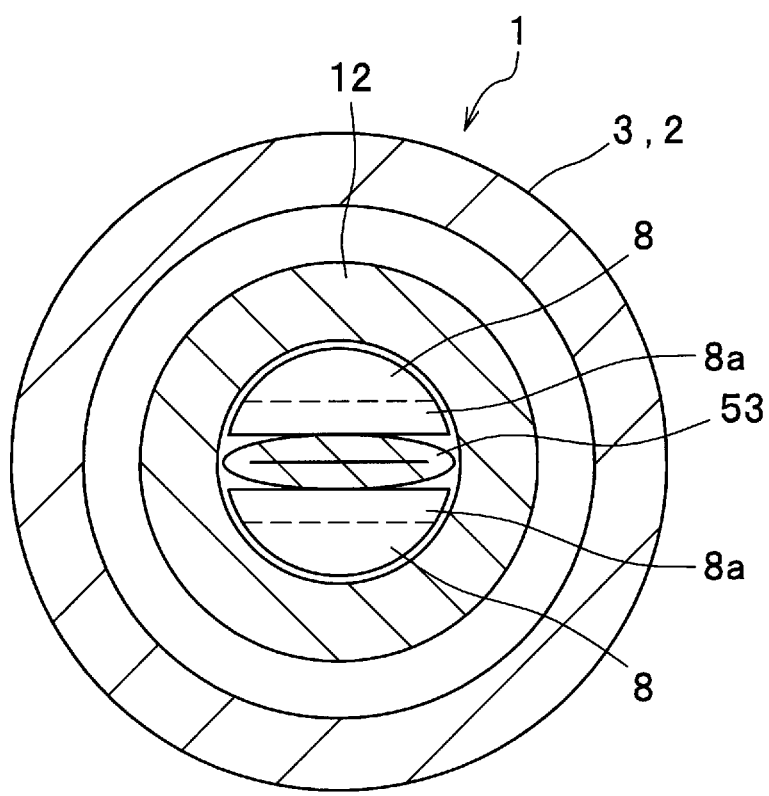
FIG. 4 is a B-B sectional view of FIG. 3.

As shown in FIGS. 3 and 4, in the protector 1, when the puncture device 50 is housed in the outer tube lumen 4, preferably after the hub 52 is held in the outer tube lumen 4 to house the needle tube 51 in the outer tube lumen 4, by the movement of the inner tube 9 in a distal end direction of the outer tube 2 (to the side of the extended part 8), the inner surface of the lumen inclined part 12 is abutted against the at least one extended part 8. Then, the extended part 8 is biased by the lumen inclined part 12 in the direction in which the diameter of the tube 53 is reduced.

With this configuration, in the protector 1, the tube 53 is occluded when the puncture device 50 is discarded after a blood collection, a blood transfusion, and the like are finished. As a result, a leak and a scatter of the blood remaining in the tube 53 from a distal end opening (the distal end opening 4a of the outer tube main body 3) can be reliably prevented. In addition, since the needle tip 51a of the puncture device 50 is housed in the outer tube 2, an erroneous puncture with the puncture device 50 can also be prevented. As a result, the protector 1 according to the present invention can further decrease contamination, infection, and the like through the blood, compared to the conventional protector.

The protector 1 shown in FIG. 3 preferably includes a lock mechanism which prevents the inner tube 9 from moving backward to the proximal end side, to keep the tube 53 occluded. Examples of configurations of the lock mechanism include the following.

Figure 6A:
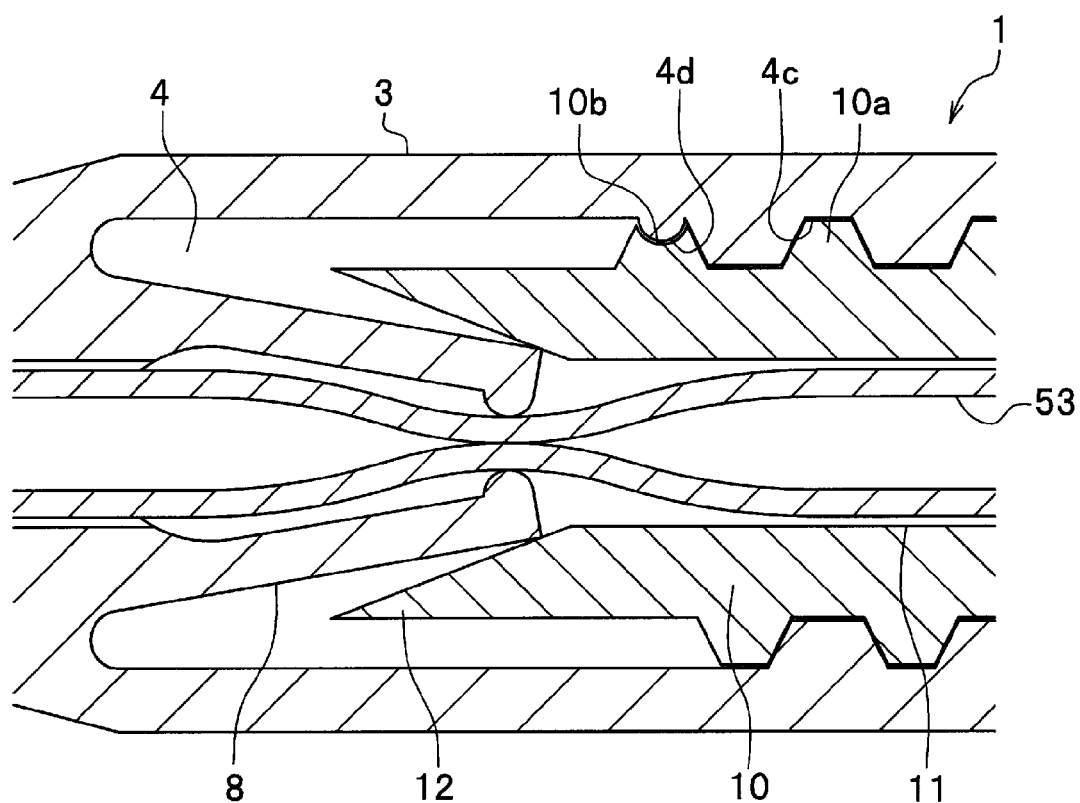
FIGS. 6(*a*) and 6(*b*) are views showing a configuration of a lock mechanism of the protector, wherein FIG. 6(*a*) is a vertical sectional view and FIG. 6(*b*) is a cross-sectional view.

As shown in FIG. 6(a), a recess part 10b is provided to a part of the male screw 10a formed on the inner tube main body 10, and a salient part 4d is provided to a part of the female screw 4c formed in the outer tube main body 3. When the tube 53 is occluded with the extended part 8, the salient part 4d is fitted into the recess part 10b.

Figure 6B:
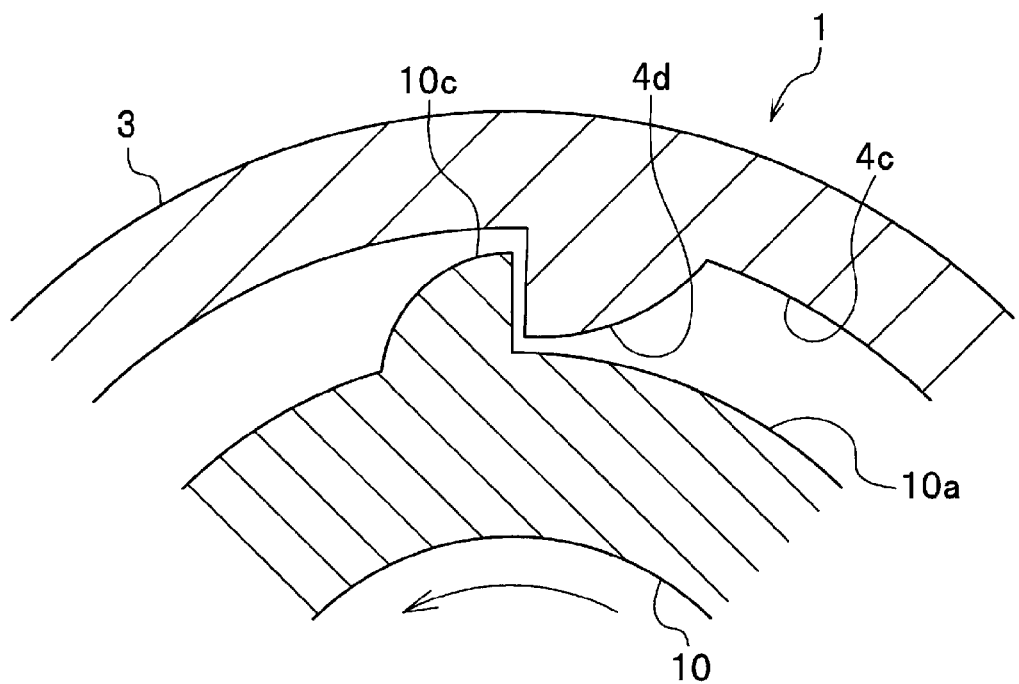

As shown in FIG. 6(b), a salient part 10c is provided to a part of the male screw 10a formed on the inner tube main body 10, and a salient part 4d is provided to a part of the female screw 4c formed in the outer tube main body 3. When the tube 53 is occluded with the extended part 8 (see FIG. 3), the salient part 10c is locked to the salient part 4d.

Figure 7A:
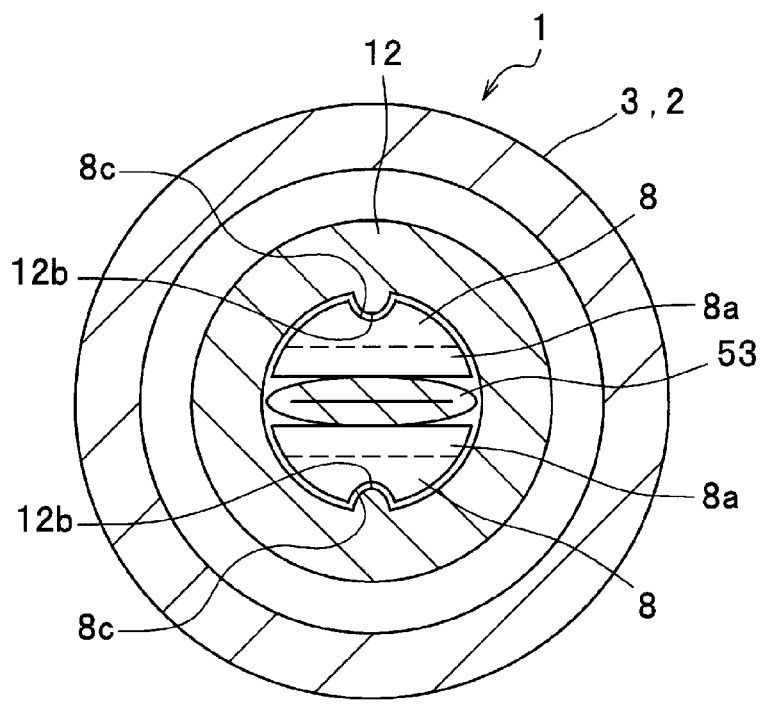
FIGS. 7(*a*) and 7(*b*) are views showing a configuration of a lock mechanism of the protector, wherein FIG. 7(*a*) is a cross-sectional view and FIG. 7(*b*) is a vertical sectional view.

As shown in FIG. 7(a), a recess part 8c is provided to a part of the extended part 8 extended to the outer tube lumen 4 (see FIG. 3), and a salient part 12b is provided to a part of the lumen inclined part 12 formed in the inner tube main body 10 (see FIG. 3). When the tube 53 is occluded with the extended part 8, the salient part 12b is fitted into the recess part 8c.

Figure 7B:
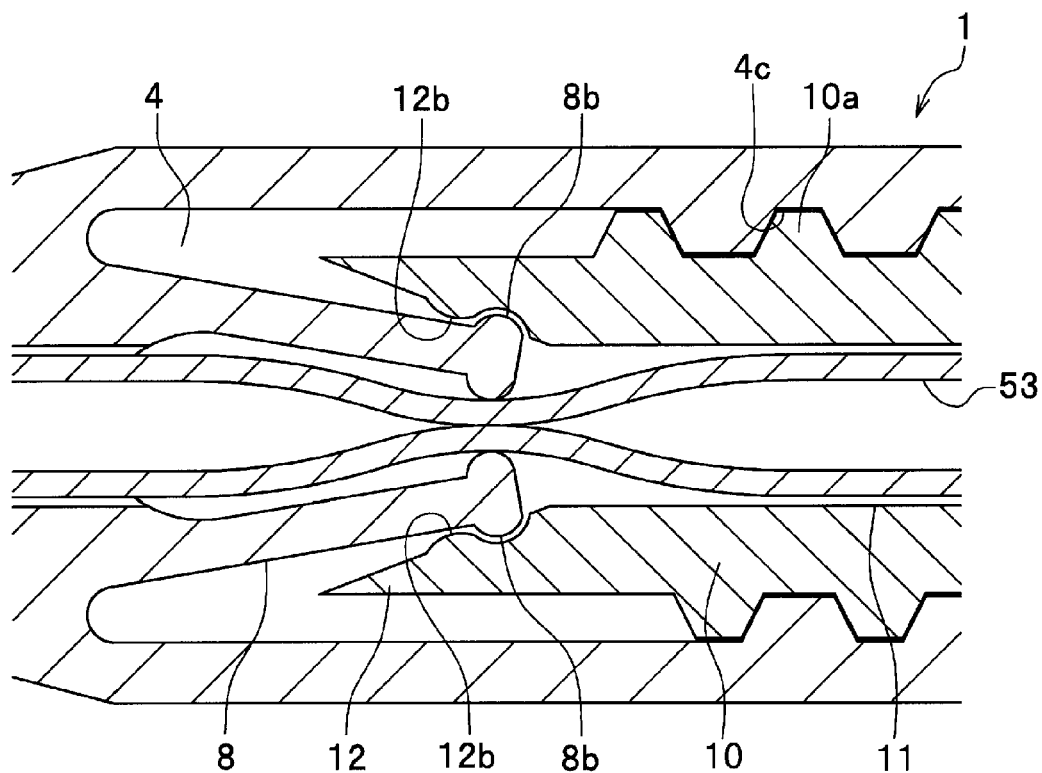

As shown in FIG. 7(b), a salient part (protruded part 8b) is provided to a part of the extended part 8 extended to the outer tube lumen 4, and the salient part 12b is provided to a part of the lumen inclined part 12 formed in the inner tube main body 10. When the tube 53 is occluded with the extended part 8, the salient part 12b is locked to the salient part 8b.

Note that, in the protector 1 shown in FIG. 3, a recess part (not shown) may be provided to a part of the operation part 13 of the inner tube main body 10, and a salient part (not shown) may be provided to a part of a proximal end of the outer tube main body 3. When the tube 53 is occluded with the extended part 8, the outer tube main body 3 may be fitted into the operation part 13.

Also, a salient part (not shown) may be provided to a part of an outer surface of the inner tube main body 10 on which the male screw 10a is not formed, and a salient part (not shown) may be provided to a part of an inner surface of the outer tube main body 3 in which the female screw 4c is not formed. When the tube 53 is occluded with the extended part 8, the inner tube main body 10 may be locked to the outer tube main body 3.

Second Embodiment of Protector

A second embodiment of a protector according to the present invention will be described with reference to the drawings.

Figure 8:
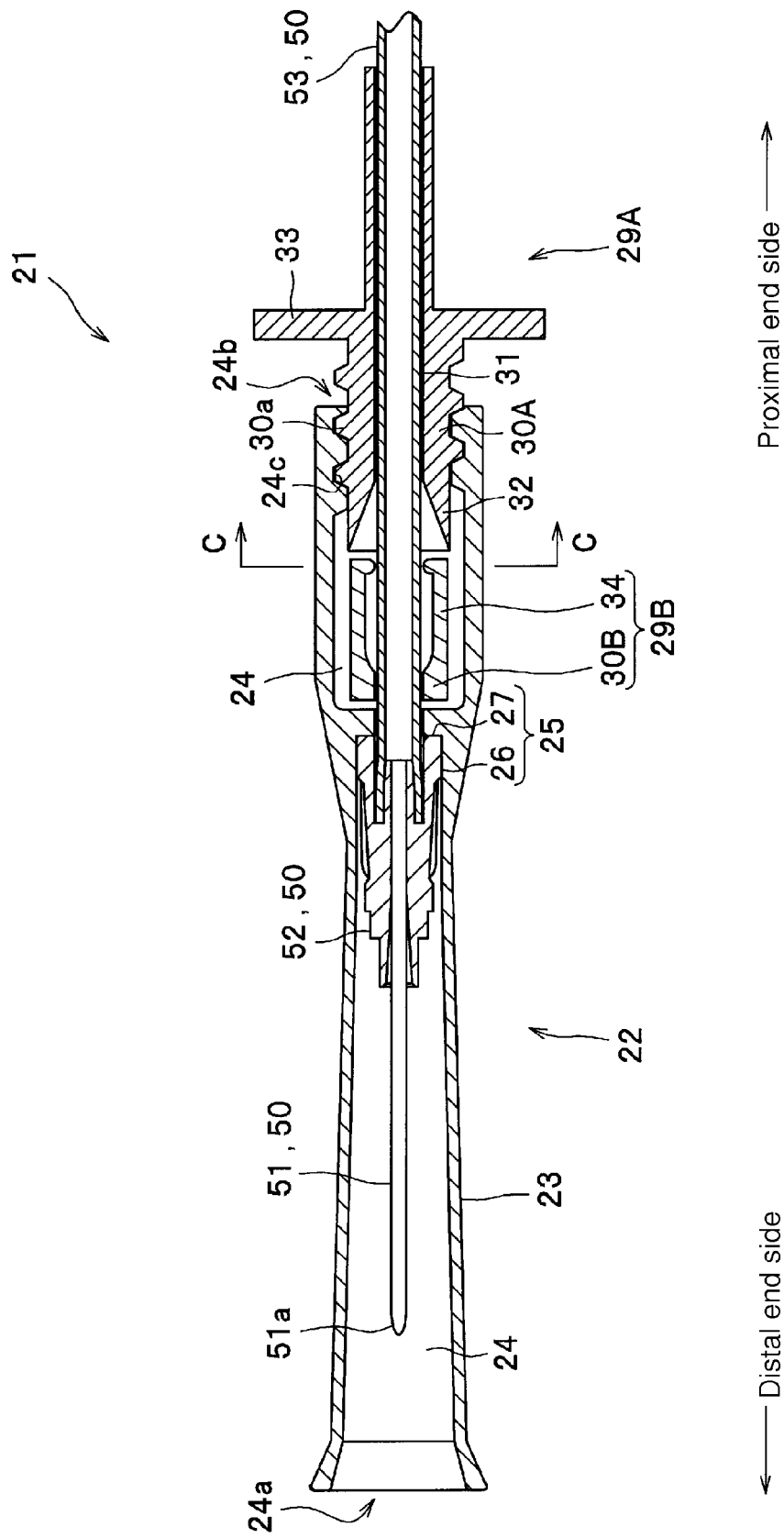
FIG. 8 is a vertical sectional view showing a configuration of a protector according to a second embodiment before an occlusion of a tube.

As shown in FIGS. 8 and 12, like the protector 1 of the first embodiment, a protector 21 of the second embodiment is used by being attached to a puncture device 50, and movable in a longitudinal direction of a tube 53.

Figure 9:
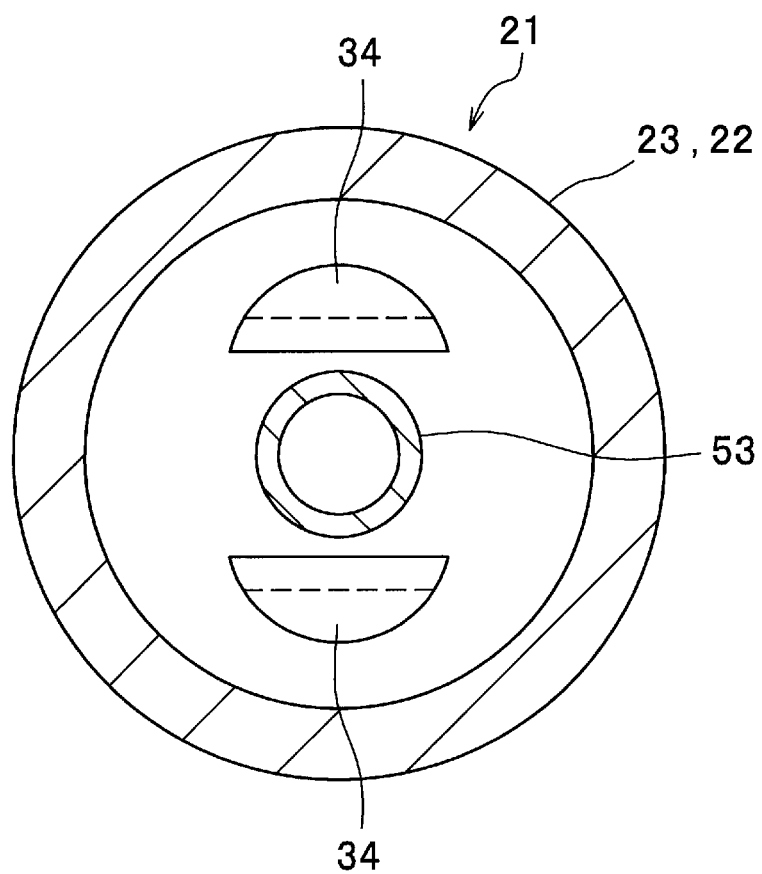
FIG. 9 is a C-C sectional view of FIG. 8.

As shown in FIGS. 8 and 9, in the protector 21 of the second embodiment, the inner tube 9 of the protector 1 of the first embodiment (see FIGS. 1 and 2) is replaced with a first inner tube 29A and a second inner tube 29B. The first inner tube 29A functions in a similar manner to the inner tube 9 and the second inner tube 29B functions in a similar manner to the extended part 8 of the outer tube 2.

The protector 21 includes an outer tube 22, the first inner tube 29A, and the second inner tube 29B.

A material for the outer tube 22, the first inner tube 29A, and the second inner tube 29B is not particularly limited but can include, for example, polyolefin such as polyethylene, polypropylene, and ethylene-vinyl acetate copolymer, and various synthetic resin materials such as polycarbonate. In the following, each of the configurations will be described.
(Outer Tube)

The outer tube 22 includes an outer tube main body 23 and a holding part 25. Since the outer tube main body 23 and the holding part 25 are similar to the outer tube main body 3 and the holding part 5 of the protector 1 of the first embodiment, respectively, the description thereof is omitted.

Note that, in the outer tube main body 23, an outer tube lumen 24 is formed like the first embodiment. Both ends of the outer tube lumen 24 are opened, and a distal end opening 24a and a proximal end opening 24b are included in the outer tube lumen 24. The outer tube lumen 24 houses the puncture device 50 inside. Also, the holding part 25 includes a reduced diameter part 26 and a step part 27 which are respectively similar to the reduced diameter part 6 and the step part 7 of the first embodiment. The holding part 25 includes either the reduced diameter part 26 or the step part 27.
(First Inner Tube)

The first inner tube 29A includes a first inner tube main body 30A and a lumen inclined part 32. In the first inner tube main body 30A, an inner tube lumen 31 is formed. Since the first inner tube main body 30A (inner tube lumen 31) and the lumen inclined part 32 are similar to the inner tube main body 10 (inner tube lumen 11) and the lumen inclined part 12 of the first embodiment, respectively, the description thereof is omitted.

Note that the first inner tube main body 30A preferably includes an operation part 33 and a male screw 30a which are similar to the operation part 13 and the male screw 10a of the first embodiment, respectively. In addition, the outer tube main body 23 (outer tube lumen 24) includes a female screw 24c when the first inner tube main body 30A includes the male screw 30a.
(Second Inner Tube)

The second inner tube 29B includes a second inner tube main body 30B and an extended part 34.

The second inner tube main body 30B includes a tubular body, both ends of which are opened. The tube 53 is inserted into the tubular body. The second inner tube main body 30B is held in a distal end direction of the first inner tube 29A in the outer tube lumen 24. In addition, preferably, the second inner tube main body 30B is held by surface contact between an outer periphery thereof and an inner periphery of the outer tube main body 23 (outer tube lumen 24). Also, by the movement of the first inner tube 29A, which will be described later, the second inner tube main body 30B is moved in a distal end direction of the outer tube 22, and abutted against the holding part 25 (outer tube 22).

The extended part 34 is extended from a proximal end side of the second inner tube main body 30B toward the lumen inclined part 32 in a proximal end direction of the outer tube lumen 24. At least one extended part 34 is formed on an end surface peripheral rim of the proximal end side of the second inner tube main body 30B. Multiple extended parts 34 are preferably formed at regular intervals. As described later, the extended part 34 is abutted against the inner surface of the lumen inclined part 32 by the movement of the first inner tube 29A and biased by the lumen inclined part 32 in a direction in which the diameter of the tube 53 is reduced. Also, the extended part 34 is similar to the extended part 8 of the first embodiment, excluding what has been described above.

Figure 10:
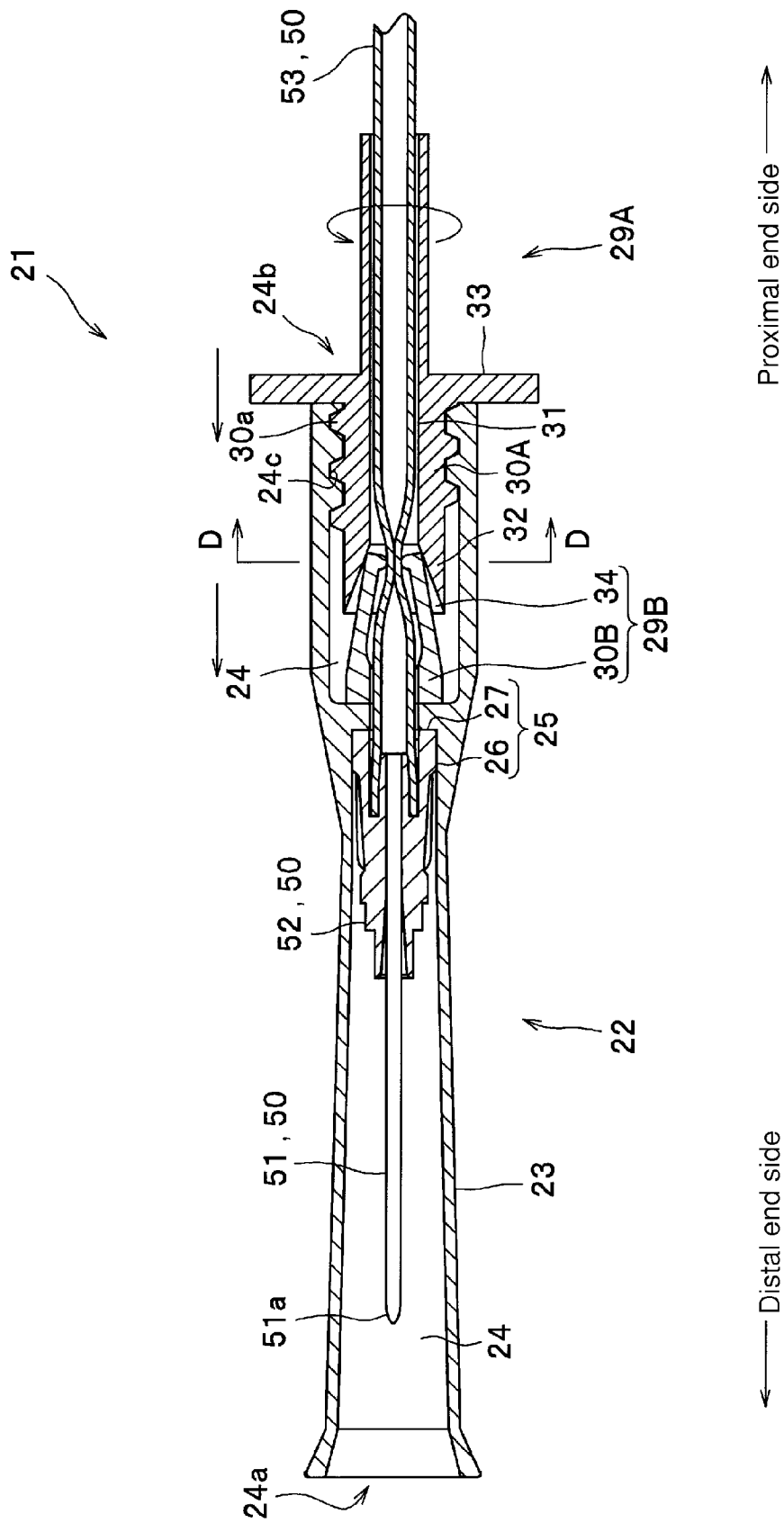
FIG. 10 is a vertical sectional view showing a configuration of the protector according to the second embodiment after the occlusion of the tube.
Figure 11:
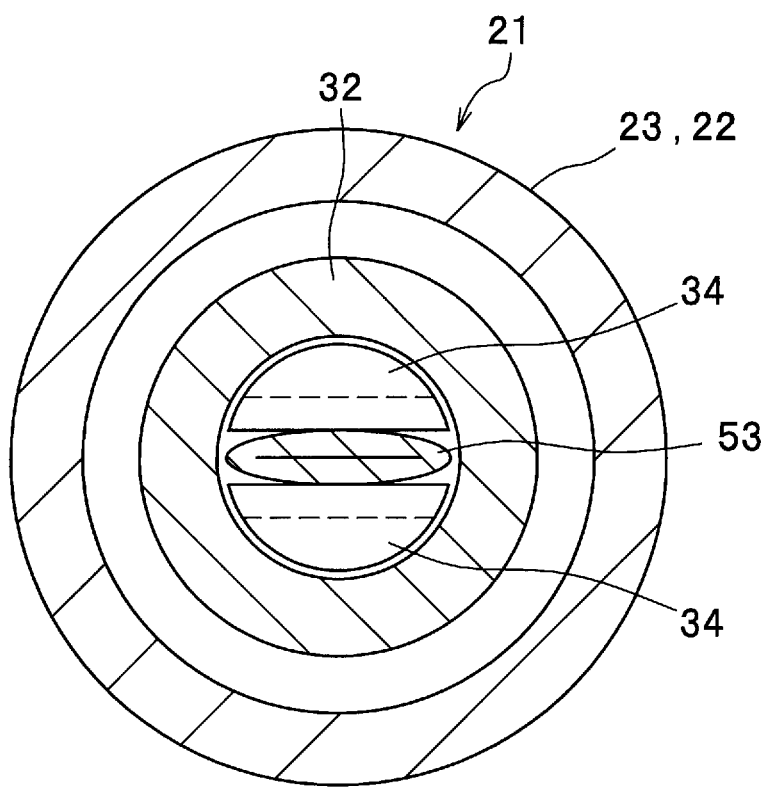
FIG. 11 is a D-D sectional view of FIG. 10.

As shown in FIGS. 10 and 11, in the protector 21, when the puncture device 50 is housed in the outer tube lumen 24, preferably after the hub 52 is held in the outer tube lumen 24 to house the needle tip 51a of the needle tube 51 in the outer tube lumen 24, by the movement of the first inner tube 29A in the distal end direction of the outer tube 22, the second inner tube 29B is moved in the distal end direction of the outer tube 22 and abutted against the holding part 25. Then, the inner surface of the lumen inclined part 32 is abutted against the at least one extended part 34, and the extended part 34 is biased by the lumen inclined part 32 in the direction in which the diameter of the tube 53 is reduced.

With the configuration described above, in the protector 21, the tube 53 is occluded when the puncture device 50 is discarded after a blood collection, a blood transfusion, and the like are finished. As a result, a leak and a scatter of the blood remaining in the tube 53 from a distal end opening (the distal end opening 24a of the outer tube main body 23) can be reliably prevented. In addition, since the needle tip 51a of the puncture device 50 is housed in the outer tube 22, an erroneous puncture with the puncture device 50 can also be prevented. As a result, the protector 21 according to the present invention can further decrease contamination, infection, and the like through the blood, compared to the conventional protector.

<Blood Bag System>

Next, a blood bag system including a puncture device to which a protector is attached will be described. Examples of the blood bag system include one having a configuration shown in FIG. 12.

A blood bag system 100 includes the puncture device 50, a blood collecting bag 101, a blood treatment filter 102, a blood preservation bag 103, a blood preservation bag 104, a medical solution-filled bag 105, and connecting tubes 106a to 106e. The protector 1 (21) according to the present invention is attached to the puncture device 50. The connecting tubes 106a to 106e respectively connect the elements of the blood bag system 100.

The blood collecting bag 101 is connected to the tube 53 of the puncture device 50, collects the blood from a blood donor through the tube 53 and stores the collected blood.

The blood treatment filter 102 separates prescribed blood components (such as white blood cells and platelets) from the blood (whole blood) transferred from the blood collecting bag 101 through the connecting tube 106a.

Through the connecting tube 106b, the blood preservation bag 103 collects the blood, which has passed through the blood treatment filter 102 and from which the prescribed blood components have been removed. Also, a clamp 111b is provided to the connecting tube 106b. The clamp 111b occludes a flow channel of the connecting tube 106b.

A blood component (blood plasma) which is centrifuged in the blood preservation bag 103 is transferred to the blood preservation bag 104 through the connecting tubes 106c and 106d, and a branch pipe 107.

A medical solution (red blood cell preservation solution) is filled in the medical solution-filled bag 105. The red blood cell preservation solution is transferred to the blood preservation bag 103 through the connecting tubes 106e and 106c, and the branch pipe 107. Then the red blood cell preservation solution is added to a blood component (red cell concentrate) remaining in the blood preservation bag 103 after the centrifugation.

Outlets 108 are formed on upper parts of the blood preservation bag 103 and the blood preservation bag 104. Also, the outlets 108 may be provided to the blood collecting bag 101 and the medical solution-filled bag 105, if necessary. In addition, labels 109 are affixed to the respective bags 101, 103, 104, 105 to show the blood components to be filled in the bags. Furthermore, flow channel sealers, which are not shown, are provided to the connecting tubes 106a to 106e, when needed. The flow channel sealers are provided to block (seal) the flow channels of the connecting tubes. When the flow channel sealers are broken, the flow channels are opened.

A test blood bag 110 may be provided to the blood bag system 100.

The test blood bag 110 collects and stores initial flow blood upon a blood collection. The test blood bag 110 is connected to a branch connector 112 provided on the way of the tube 53 through a branch tube 106f. Also, a clamp 111a is provided to the branch tube 106f. The clamp 111a occludes a flow channel of the branch tube 106f. In addition, a flow channel sealer 113 is provided to the branch connector 112 on the side of the blood collecting bag 101. The flow channel sealer 113 prevents the initial flow blood from flowing into the blood collecting bag during the collection of the initial flow blood. Furthermore, a sampling port 114 is connected to the test blood bag 110. The blood to be tested is collected through the sampling port 114 to a pressure-reduced blood collecting tube which is not shown. The sampling port 114 includes a needle assembly 115 and a holder 116. The holder 116 houses the pressure-reduced blood collecting tube inside and connects the pressure-reduced blood collecting tube to the needle assembly 115.

<Method for Using Protector>

Examples of a method for using a protector will be described with reference to a blood treatment method using the above-described blood bag system 100 shown in FIG. 12.

(1) The protector 1 (21) is brought to the first condition in which the protector 1 (21) is spaced from the hub 52. Also, the clamp 111a is not closed and the branch tube 106f is kept opened. A blood collection is started in this condition with the needle tube 51 puncturing a blood vessel of a blood donor. Here, the initial flow blood is collected into the test blood bag 110 through the tube 53 and the branch tube 106f.

(2) After a prescribed amount of the initial flow blood is collected into the test blood bag 110, the clamp 111a is closed and the branch tube 106f is occluded. Also, the tube 53 is opened by breaking the flow channel sealer 113 and opening the flow channel. As a result, the blood from which initial flow blood has been removed is collected into the blood collecting bag 101 through the tube 53.

(3) After a prescribed amount of the blood is collected into the blood collecting bag 101, the needle tube 51 is pulled out of the blood vessel of the blood donor and the blood collection is finished.

(4-1) First Step and Second Step

The protector 1 (21) is moved to the side of the hub 52, or the tube 53 is pulled to the side of the blood collecting bag 101. Thus, the hub 52 (needle tube 51) is pulled back and the protector 1 (21) is brought to the second condition in which the puncture device 50 is housed and held in the outer tube lumen 4 (24) (see FIGS. 1 and 8).

(4-2) Third Step

With the puncture device 50 housed in the outer tube lumen 4 (24), the inner tube 9 (first inner tube 29A and second inner tube 29B) of the protector 1 (21) is moved in the distal end direction of the outer tube 2 (22) (see FIGS. 3, 4, 10, and 11). Note that the movement of the inner tube 9 (first inner tube 29A) is preferably a rotational movement by a screw fit.

(4-3) Fourth Step

The inner tube 9 (first inner tube 29A and second inner tube 29B) is moved in the distal end direction of the outer tube 2 (22). Then, the extended part 8 (34) is abutted against the inner surface of the lumen inclined part 12 (32) and biased in the direction in which the diameter of the tube 53 is reduced, along with and by the lumen inclined part 12 (32) (see FIGS. 3, 4, 10, and 11).

(4-4) Fifth Step

When the extended part 8 (34) is biased in the direction in which the diameter of the tube 53 is reduced, the tube 53 is deformed and a lumen of the tube 53 is occluded (see FIGS. 3, 4, 10, and 11).

(5) The tube 53 and the branch tube 106f are sealed by fusion welding with a tube sealer and the like. Then, the puncture device 50 and the test blood bag 110 are cut off from the blood collecting bag 101, and then, the puncture device 50 is discarded.

Here, in the puncture device 50, the needle tube 51 (needle tip 51a) is covered with the protector 1 (21) and the tube 53 is occluded. As a result, an erroneous puncture can be prevented, and a leak and a scatter of the blood can also be prevented.

(6) Through the blood treatment filter 102, white blood cells, platelets, and the like are separated from the blood collected in the blood collecting bag 101, and the remaining blood components are collected into the blood preservation bag 103. Then, the clamp 111b is closed and the connecting tube 106b is occluded, and then the connecting tube 106b is sealed by fusion welding with a tube sealer and the like. Then, the blood collecting bag 101 and the blood treatment filter 102 are cut off from the blood preservation bag 103.

(7) The blood preservation bag 103 is centrifuged, and the blood in the blood preservation bag 103 is separated into a red blood cell layer and a blood plasma layer. The blood plasma is transferred into the blood preservation bag 104. Then, the medical solution (red blood cell preservation solution) is added from the medical solution-filled bag 105 to the concentrated red blood cells remaining in the blood preservation bag 103 and mixed therewith. As a result, a red cell concentrate is prepared in the blood preservation bag 103, and platelet poor plasma is prepared in the blood preservation bag 104.

REFERENCE SIGNS LIST 1 protector
2 outer tube
3 outer tube main body
4 outer tube lumen
5 holding part
8 extended part
9 inner tube
10 inner tube main body
11 inner tube lumen
12 lumen inclined part
21 protector
22 outer tube
23 outer tube main body
24 outer tube lumen
25 holding part
29A first inner tube
29B second inner tube
30A first inner tube main body
30B second inner tube main body
31 inner tube lumen
32 lumen inclined part
34 extended part
50 puncture device
51 needle tube
52 hub
53 tube

The invention claimed is:

1. A protector configured to be used by being attached to a puncture device including a needle tube which includes a needle tip on a distal end side thereof, a hub provided to a proximal end side of the needle tube, and a tube connected to a proximal end side of the hub and communicating with the needle tube through the hub, the protector being movable in a longitudinal direction of the tube, the protector comprising:
an outer tube including:
a tubular outer tube main body which includes an outer tube lumen configured to house the puncture device;
a holding part configured to hold the hub in the outer tube lumen to house the needle tip in the outer tube lumen; and
an inner tube including:
a tubular inner tube main body which is held in a proximal end side of the outer tube lumen and movable in a distal end direction of the outer tube lumen and includes an inner tube lumen into which the tube is inserted;
said protector further comprising:
at least one extended part formed as part of said outer tube; and
a lumen inclined part having an inner diameter that gradually increases towards said at least one extended part thereby forming an inner inclined surface,
wherein, when the puncture device is housed in the outer tube lumen, the inner tube is moved in a distal end direction of the outer tube, whereby said inner surface of the lumen inclined part is abutted against the extended part and the extended part is biased by the lumen inclined part in a direction in which a diameter of the tube is reduced.

2. The protector according to claim 1 wherein said at least one extended part is extended from a proximal end side of the holding part in a proximal end direction of the outer tube lumen and said lumen inclined part is adjacent said inner tube lumen.

3. A method for using the protector according to claim 1, comprising:
housing the puncture device in the outer tube lumen;
holding the puncture device in the outer tube lumen;
moving the inner tube in the distal end direction of the outer tube with the puncture device housed in the outer tube lumen;
abutting the extended part against the inner surface of the lumen inclined part after the inner tube is moved in the distal end direction of the outer tube, and then biasing the extended part along with and by the lumen inclined part in the direction in which the diameter of the tube is reduced; and
deforming the tube and occluding a lumen of the tube by biasing the extended part in the direction in which the diameter of the tube is reduced.

4. A protector configured to be used by being attached to a puncture device including a needle tube which includes a needle tip on a distal end side thereof, a hub provided to a proximal end side of the needle tube, and a tube connected to a proximal end side of the hub and communicating with the needle tube through the hub, the protector being movable in a longitudinal direction of the tube, the protector comprising:
an outer tube including:
a tubular outer tube main body which includes an outer tube lumen configured to house the puncture device; and
a holding part configured to hold the hub in the outer tube lumen to house the needle tip in the outer tube lumen;
a first inner tube including:
a tubular first inner tube main body which is held in a proximal end side of the outer tube lumen and movable in a distal end direction of the outer tube lumen and includes an inner tube lumen into which the tube is inserted; and
a second inner tube including:
a tubular second inner tube main body which is held in a distal end direction of the first inner tube in the outer tube lumen and movable in the distal end direction of the outer tube lumen, and into which the tube is inserted;
said protector further comprising:
at least one extended part;
a lumen inclined part having an inner diameter that gradually increases toward said at least one extended part thereby forming an inner inclined surface; and
wherein when the puncture device is housed in the outer tube lumen, the first inner tube is moved in a distal end direction of the outer tube, whereby the second inner tube is moved in the distal end direction of the outer tube and abutted against the holding part, said inner inclined surface of the lumen inclined part is abutted against the extended part, and the extended part is biased by the lumen inclined part in a direction in which a diameter of the tube is reduced.

5. The protector according to claim 4 wherein said at least one extended part is extended from a proximal end side of the second inner tube main body in a proximal end direction of the outer tube lumen and said lumen inclined part is adjacent said inner tube lumen.

6. A method for using the protector according to claim 4, comprising:
- housing the puncture device in the outer tube lumen;
- holding the puncture device in the outer tube lumen;
- moving the first inner tube in the distal end direction of the outer tube, with the puncture device housed in the outer tube lumen, to move the second inner tube in the distal end direction of the outer tube;
- abutting the extended part against the inner surface of the lumen inclined part after the second inner tube is moved in the distal end direction of the outer tube, and then biasing the extended part along with and by the lumen inclined part in the direction in which the diameter of the tube is reduced; and
- deforming the tube and occluding a lumen of the tube by biasing the extended part in the direction in which the diameter of the tube is reduced.

* * * * *